(12) United States Patent
Sieverding et al.

(10) Patent No.: US 6,268,371 B1
(45) Date of Patent: Jul. 31, 2001

(54) FUNGICIDAL MIXTURES

(75) Inventors: Ewald Sieverding, St. Johann (DE); Leslie May, Wokingham (GB)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/391,794

(22) Filed: Sep. 9, 1999

Related U.S. Application Data
(60) Provisional application No. 60/099,780, filed on Sep. 10, 1998.

(51) Int. Cl.[7] .............................. A01N 43/54; A01N 37/34
(52) U.S. Cl. ............................................. 514/258; 514/521
(58) Field of Search ...................... 514/258, 521

(56) References Cited

U.S. PATENT DOCUMENTS

| | | | |
|---|---|---|---|
| 4,567,263 | 1/1986 | Eicken et al. | 544/263 |
| 5,593,996 | 1/1997 | Pees et al. | 514/258 |

FOREIGN PATENT DOCUMENTS 0 262 393 B1   8/1987   (EP) .

Primary Examiner—Allen J. Robinson
(74) Attorney, Agent, or Firm—Barbara V. Maurer

(57) ABSTRACT

The invention relates to fungicidal composition comprising an acceptable carrier and/or surface active agent and synergistically effective amounts of
(a) at least one azolopyrimidine of formula I

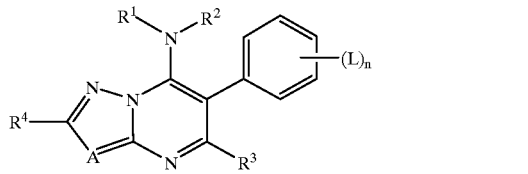

in which $R^1$ through $R^2$, L, A and n have the meaning given in claim 1;
(b) and at least one melanin biosynthesis inhibitor (MBI), preferably a phenoxyamide of formula II

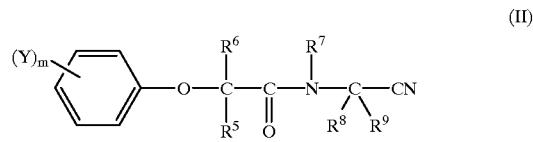

wherein $R^5$ through $R^9$, Y and m have the meaning given in claim 2; and to a method of controlling the growth of phythopathogenic fungi at a locus which comprises applying synergistically effective amounts of at least one azolopyrimidine of formula I (a) and at least one MBI (b) to the locus.

4 Claims, No Drawings

FUNGICIDAL MIXTURES

This application claims the benefit of U.S. Provisional Application No. 60/099,780, filed Sep. 10, 1998.

BACKGROUND OF THE INVENTION

The present invention relates to a fungicidal composition comprising a fungicidally acceptable carrier and/or surface active agent and synergistically effective amounts of (a) at least one azolopyrimidine of formula I in which $R^1$ and $R^2$ each independently represent hydrogen or an optionally substituted alkyl, alkenyl, alkynyl, alkadienyl, aryl, heteroaryl, cycloalkyl, bicycloalkyl or heterocyclyl group, or $R^1$ and $R^2$ together with the adjacent nitrogen atom represent an optionally substituted heterocyclic ring, $R^3$ represents a hydrogen or a halogen atom or an alkyl group, $R^4$ represents hydrogen or an alkyl or aryl group, L represents a halogen atom or an optionally substituted alkyl or alkoxy group, A represents N or $CR^5$, wherein $R^5$ has the meaning given for $R^4$, and n is 0 or an integer between 1 and 5; and (b) and at least one fungicidal active ingredient which is capable of inhibiting the melanin biosynthesis in particular in *Pyricularia oryzae* the causal agent of the rice blast disease.

The fungicidal compounds of formula I are known from U.S. Pat. No. 4,567,263 and U.S. Pat. No. 5,593,996.

The class of melanin biosynthesis inhibitors (MBI) are chemical compounds which are capable of diminishing the in-vivo synthesis of melanin by inhibiting any of the reductase and/or dehydratase enzymes which are responsible for converting tetrahydroxynaphthalene into dihydroxynaphthalene. This class of compounds includes the following known compounds: carpropamid, chlobenthiazione, diclocymet, pyroquilon, phthalide, tricyclazole and certain phenoxyamides, which are known for example from EP 0 262 393 and Japanese patent application JP 5-9165-A.

However, there is no hint to combine the compounds of formula I, with a MBI. Moreover, there is no hint that such mixtures can be advantageously be used for controlling rice diseases such as rice blast and rice sheath blight and others.

Surprisingly, a strong synergy between the compounds of formula I and MBIs in field trials was found when these two compounds were in-tank mixed and when the activity of these co-formulations was compared with that of the solo formulations of each active ingredient.

A mixture of fungicides shows synergistic effect if the fungicidal activity of the mixture is larger than the sum of activities of the separately applied compounds. The expected fungicidal activity for a given mixture of two fungicides can also be calculated as follows (See Colby, S. R., "Calculating synergistic and antagonistic response of herbicide combinations", Weeds 15, pp 20–22 (1967):

$$EE = x + y - x \cdot y / 100$$

wherein x is the efficacy in % compared with an untreated control upon treatment with a fungicidal active ingredient A at a dose rate a;

y is the efficacy in % compared with an untreated control upon treatment with a fungicidal active ingredient B at a dose rate b;

EE is the expected efficacy with a combination of fungicidal active ingredients A and B at a dose of a+b, respectively.

If the actual efficacy (E) exceeds the expected (calculated) one (EE), the mixture displays a synergistic effect.

SUMMARY OF THE INVENTION

The present invention includes a fungicidal composition comprising an acceptable carrier and/or surface active agent and synergistically effective amounts of at least one compound of formula I, and at least one melanin biosynthesis inhibitor (MBI).

The present invention also includes a method of controlling the growth of phytopathogenic fungi at a locus which comprises applying synergistically effective amounts of at least one azolopyrimidine of formula I and at least one MBI to the locus.

DETAILED DESCRIPTION OF THE PREFERRED EMBODIMENTS

Preferred compounds of formula I include those wherein $R^1$ and $R^2$ together with the interjacent nitrogen atom represent an optionally substituted 6-membered heterocyclic ring, in particular a 4-methylpiperidine ring, or wherein $R^1$ represents a $C_{1-6}$ alkyl, in particular an isopropyl group, a $C_{1-6}$ haloalkyl, in particular a 2,2,2-trifluoroethyl or a 1,1,1-trifluoroprop-2-yl group, or a $C_{3-8}$ cycloalkyl group, in particular a cyclopentyl or cyclohexyl group and $R^2$ represents a hydrogen atom or a $C_{1-6}$ alkyl group and/or wherein wherein $L^1$ represents a halogen atom, preferably flourine or chlorine and $L^2$ and $L^3$ each independently represent a hydrogen atom or a halogen atom, preferably fluorine, in particular wherein $L^1$ represents fluorine, $L^2$ represents hydrogen and $L^3$ represents chlorine or wherein $L^1$ through $L^3$ represent fluorine and/or wherein Hal represents a chlorine atom.

In a particularly preferred embodiment the azolopyrimidine is the compound of formula IA (IA)

$$\begin{array}{c} R^1 \diagdown N \diagup R^2 \\ \text{[azolopyrimidine ring with (L)}_n\text{ phenyl and Hal]} \end{array}$$

wherein L and n have the meaning given for formula I, and

R$^1$ represents an alkyl or haloalkyl group,

R$^2$ represents a hydrogen atom, or

R$^1$ and R$^2$ together represents an optionally substituted alkylene group having 3 to 6 carbon atoms in the main chain, in which one CH$_2$ group may be replaced by O or NH, and Hal denotes a halogen atom.

Particularly preferred are the following azolopyrimidines: 5-chloro-6-(2-chloro-6-fluorophenyl)-7-(4-methylpiperid-1-yl)-[1,2,4]triazolo[1,5-a]pyrimidine coded Azoloyrimidine A, 5-chloro-6-(2-chloro-6-fluorophenyl)-7-isopropylamino-[1,2,4]triazolo[1,5-a]pyrimidine coded Azoloyrimidine B, 5-chloro-6-(2-chloro-6-fluorophenyl)-7-(2,2,2-trifluoroethylamino)-[1,2,4]triazolo[1,5-a]pyrimidine coded Azoloyrimidine C and 5-chloro-6-(2,4,6-trifluorophenyl)-7-(1,1,1-trifluoroprop-2-ylamino)-[1,2,4]triazolo[1,5-a]pyrimidine coded Azoloyrimidine D.

Preferred MBIs include carpropamid, chlobenthiazione, dicyclocymet, pyroquilon, phthalide and tricyclazole.

Furthermore, the phenoxyamides of formula 11 are preferred MBIs:

(II)

$$(Y)_m\text{-phenyl-O-C(R^5)(R^6)-C(=O)-N(R^7)-C(R^8)(R^9)-CN}$$

wherein

R$^5$ and R$^6$ each independently represent a hydrogen atom or an optionally substituted alkyl group;

R$^7$ independently represents a hydrogen atom or an optionally substituted alkyl group R$^8$ and R$^9$ each independently represent a hydrogen atom or an optionally substituted alkyl or alkenyl group; or R$^8$ and R$^9$ together may represent an alkylene group;

Y each independently represents a halogen atom or an optionally substituted alkyl or alkenyl group or a cyano or nitro group;

m is 0 or an integer of 1, 2, 3 or 4.

Particularly preferred phenoxyamides are the compounds of formula IIA (IIA)

$$(Y)_m\text{-phenyl-O-CH(CH}_3\text{)-C(=O)-N(H)-C(CH}_3\text{)(R}^9\text{)-CN}$$

wherein R$^9$, Y and m have the meaning given, in particular wherein $$(Y)_m\text{-phenyl- represents Cl-[phenyl with Y' and Cl substituents]}$$

in which Y' represents a hydrogen atom or a methyl group and/or wherein

R$^9$ represents a C$_{1-8}$-alkyl group.

Most preferred are N-(1-cyano-1,2-dimethyl-propyl)-2-(2,4-dichlorophenoxy)-propionamide, in particular a mixture of (2R)-and (2R/S)-N-(1-cyano-1,2-dimethyl-propyl)-2-(2,4-dichlorophenoxy)-propionamide coded Propionamide E and N-(1-cyano-1-ethyl-propyl)-2-(2,4-dichloro-3-methylphenoxy)-propionamide coded Propionamide F.

Preferred formulations of this invention include those comprising the following constituents:

a carrier agent;

at least one azolopyrimidine of formula I, at least one MBI, in particular a phenoxyamide of formula II, optionally a foam breaking agent, in particular a mixture of perfluoroalkyphosphonic acids and/or perfluoroalkylphosphinic acids, in particular Defoamer SF or Fluowett PL, which are commercially available from Clariant GmbH.

The compound of formula I and the MBI are to be applied together, in synergistically effective amounts. These synergistic mixtures exhibit an extraordinary efficacy against a broad range of phytopathogenic fungi, in particular against fungi from the classes ascomycetes, basidiomycetes and deuteromycetes. Therefore, they can be applied advantageously against rice diseases. They are systemic and may be applied as leaf, into water, seed dressing, nursery box or soil fungicides.

The mixture according to the invention may be preferably applied for controlling phytopathogenic fungi of the genera: Pyricularia, Rhizoctonia, Cochliobolus, Cercospora, Magnaporthe, Alternaria, Drechslera, Fusarium, Gerlachia, Achlya, Sclerotium, Gibberella, Mycosphaerella, Balansia, Sarocladium, Pythium, Phoma, Phytophthora, Bipolaris, Curvularia, Sarocladium, Nigrospora, Entyloma, Sclerophthora, Cylindrocladium, Gaeumannomyces, Myrothecium, Mucor, Rhizopus, Tilletia, Ustilago, Ustilaginoidea, Bipolaris, Sclerotium, Botrytis, Venturia, Erysiphe, Septoria, Puccinia, Leptosphaeria and Pseudocercosporella, in particular the species *Rhizoctonia solani, Cochliobolus miyabeanus, Spharulina oryzina, Leptosphaeria slavini* and *Pyricularia oryzae*.

The application rate of the compound of formula I according to this invention is usually in the range of 5 to 2000 grams of active ingredient (g a.i.) per hectare, with rates between 30–500 g a.i./ha often achieving satisfactory control. The optimal rate for a specific application will depend on the crop(s) under cultivation and the predominant species of infesting fungus, and readily may be determined by established biological tests known to those skilled in the art.

In general, the preferred application rate of the compounds of formula I is in the range of 10 to 500 g a.i./ha, more preferably 30–300 g a.i./ha.

The optimal rate for the MBI will depend on the crop(s) under cultivation and the level of infestation by the fungus, and can readily be determined by established biological tests.

The ratio (by weight) of the compound of formula I to the MBI is as a rule, from 1:100 to 100:1. The preferred ratio formula I: MBI may vary, e.g., from about 1:50 to about 50:1, in particular from about 1:4 to about 4:1.

The active compounds will be formulated together in a suitable ratio according to the present invention, together with usual carriers and/or additives known in the art.

Accordingly the invention further provides a fungicidal composition which comprises a carrier and, as active ingredient, at least one compound of formula I as defined above and at least one MBI.

A method of making such a composition is also provided which comprises bringing the compound of formula I and the MBI as defined above into association with at least one carrier. It is also envisaged that different isomers or mixtures of isomers of the compound of formula I and/or the MBI may have different levels or spectra of activity and thus compositions may comprise individual isomers or mixtures of isomers.

A composition according to the invention preferably contains from 0.1% to 99.9%, preferably 0.2 to 80% by weight (w/w) of active ingredients.

A carrier in a composition according to the invention is any material with which the active ingredient is formulated to facilitate application to the locus to be treated, which may for example be a plant, seed, foliage, soil, or into the water where the plant grows, or to the roots, or to facilitate storage, transport or handling. A carrier may be a solid or a liquid, including material which is normally a gas but which has been compressed to form a liquid.

The compositions may be manufactured into, e.g., emulsion or emulsifiable concentrates, solutions, oil in water emulsions, wettable powders, soluble powders, suspension concentrates, solutions, dusts, granules, water dispersible granules, tablets, aerosols, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite or others. The physical properties may be improved by addition of highly dispersed silica gel or polymers. Carriers for granules may be porous material, e.g. pumice, kaolin, sepiolite, bentonite; non-sorptive carriers may be calcite or sand or others. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

Wettable powders of this invention suitably will contain 5 to 90% w/w of active ingredient and, in addition to a solid inert carrier, 3 to 10% w/w of dispersing and wetting agents and, where necessary, 0 to 10% w/w of stabilizer(s) and/or other additives such as penetrants or stickers. Dusts may be formulated as a dust concentrate having a similar composition to that of a wettable powder but without a dispersant, and may be diluted in the field with further solid carrier to give a composition usually containing 0.5 to 10% w/w of active ingredient. Water dispersible granules and granules may have a size between 0.15 mm and 2.0 mm and may be manufactured by a variety of techniques. Generally, these granules will contain 0.5 to 90% w/w active ingredient and 0 to 20% w/w of additives such as stabilizer, surfactants, slow release modifiers and binding agents. Emulsifiable concentrates may contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are suitably milled so as to obtain a stable, non-sedimenting, flowable product and typically contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be dissolved in the formulation to assist in preventing sedimentation and crystalization or as antifreeze agents.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity, the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations which can be used according to the invention are:

| SC-A | | |
|---|---|---|
| active ingredient | Azolopyrimidine A | 100.0 g |
| Dispersing agent | Morwet D425[1] | 25.0 g |
| Dispersing agent | Pluronic ® PE10500[2] | 5.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |
| SC-B/SC-D | | |
| active ingredient | Azolopyrimidine B or D | 100.0 g |
| Dispersing agent | Soprophor ® FL[3] | 30.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxe ® I GXL[4] | 1.0 g |
| Water | | to 1000 ml |
| SC-E | | |
| active ingredient | Propionamide E | 200.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |
| SC-A/E | | |
| active ingredient | Azolopyrimidine A | 60.0 g |
| active ingredient | Propionamide E | 120.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |
| DC-A | | |
| active ingredient | Azolopyrimidine A | 100.0 g |
| Wetting agent | Pluronic ® PE6400[2] | 50.0 g |
| Dispersing agent | Lutensol ® TO 12[2] | 50.0 g |
| Solvent | benzyl alcohol | to 1000 ml |
| DC-B | | |
| active ingredient | Azolopyrimidine B | 100.0 g |
| Wetting agent | Pluronic ® PE6400[2] | 50.0 g |
| Dispersing agent | Lutensol ® TO 12[2] | 50.0 g |
| Solvent | benzyl alcohol | to 1000 ml |

[1] Product commercially available from Witco
[2] Product commercially available from BASF AG, Germany
[3] Product commercially available from Rhone-Poulenc
[4] Product commercially available from Zeneca The formulation SC-E comprising Propionamide E is in-tank mixed with any of the other formulations SC-A, SC-B, SC-D, DC-A or DC-B which comprise the Azolopyrimidines A, B or D.

In a preferred embodiment the active ingredients are added to the tank mix together, each as a solo formulation.

Therefore, the present invention relates to a kit for the preparation of a spray mixture consisting of two separate formulations:

(i) a formulation which comprises at least one azolopyrimidine of formula I, in particular Azolopyrimidines A, B, C or D, conventional adjuvants and carriers;

(ii) a formulation which comprises at least one MBI, preferably a phenoxyamide of formula II, in particular Propionamide E or F, conventional adjuvants and carriers.

In a preferred embodiment the kit includes two bottles with dispensing means which allow easy and correct addition of the formulations (i) and (ii) to the tank mix.

The formulation SC-A/E comprising Azolopyrimidine A and Propionamide E can be used directly for preparing the tank mix according to the present invention.

A composition according to the invention preferably contains from 0.5% to 95% by weight of active ingredients.

The compositions of this invention may be diluted down to a concentration of 0.0001% of active ingredients.

The compositions of this invention can be applied to the plants or their environment simultaneous with or in succession with other active substances. These other active substances can be either fertilizers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

Examples of the other fungicidal compounds are anilazine, azoxystrobin, benalaxyl, benomyl, binapacryl, bitertanol, biasticidin S. Bordeaux mixture, bromuconazole, bupirimate, captafol, captan, carbendazim, carboxin, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, iprovalicarb, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, polyoxin D, polyram, probenazole, prochloraz, procymidone, propamocarb, propiconazole, propineb, pyrazophos, pyrifenox, pyrimethanil, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, toiclofosmethyl, tolylfluanid, triadimefon, triadimenol, triazbutil, triazoxide, tridemorph, triflumizole, triforine, triticonazole, validamycin A, vinclozolin, XRD-563, zarilamid, zineb, ziram.

Examples of insecticidal compounds are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethyinon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

Examples of biological control agents are: Bacillus thuringiensis, Verticillium lecanii, Autographica californica NPV, Beauvaria bassiana, Ampelomyces quisqualis, Bacilis subtilis, Pseudomonas fluorescens, Steptomyces griseoviridis and Trichoderma harzianum.

Examples of chemical agents that induce systemic acquired resistance in plants such are: isonicotinic acid or derivatives thereof, 2,2-dichloro-3,3-dimethylcyclopropylcarboxylic acid and BION.

The present invention is of wide applicability in the protection of crop and ornamental plants against fungal attack. Preferred crop is rice and in particular paddy-rice. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLES

For the field study formulated Azolopyrimidine A, B or D (100 g/l DC-A or DC-B; 100 g/l SC-D) and formulated Propionamide E (200 g/l SC-E) were used.

The field tests of the method of the present invention were conducted on rice fields in the Philippines, in Brazil and Japan.

Materials and Application Method:

Rice seed of variety 'IR-50' was sown in a sand/garden soil in 0.07 sq.m. (0.23×0.3 m) plastic boxes. Fourteen days later, in the Z14/20 growth stage, the plants were sprayed with the fungicidal compounds for the first time. The formulated compounds were weighed out and diluted with water. Equivalents of 100, 200 and 400 g active ingredients per ha were applied with a hand hold atomizer using 1000 l spray volume per ha. The doses of the single compounds and of the mixtures are given in the tables of results below. There were three replicated boxes per treatment. The spraying was repeated 7 days after the first application using the same compounds/compound mixtures at the same dose rates and spray volume/ha.

Evaluation of the Disease:

Assessments of the rice blast disease and the rice sheath blight disease took place 14 days after the first application (=7 days after the second application) of the compounds. Percent leaf area infected was evaluated. The efficacy of the compounds/compounds mixtures to control the diseases was calculated by using the formula:

$$\% \text{ disease control} = 100 - \frac{\% \text{ disease in treated plants}}{\% \text{ disease in untreated plants}} \times 100\%$$

Determination of Synergy:

Synergy was calculated using the % disease control values of specific treatments for the two COLBY formula given hereinabove

Example 1 Control of rice blast caused by *Pyricularia oryzae*

Infection with *Pyricularia oryzae*:

Three hours after the first compound application (when the plants were dry) an in-vitro grown conidial suspension of *Pyricularia oryzae* was inoculated onto the foliar surfaces of the rice plants using a hand held atomizer. The conidial concentration was about 1 million per ml. Plants were then placed into a moist chamber for 24 h at 24–26 degree C. with about 100% relative humidity. The plants were then moved outdoors until the rice blast disease could be evaluated.

The formulations applied, the dosage rates of the active ingredients applied (expressed in grams of active ingredient per hectare), the results expressed as efficacy of disease control and the expected efficacies calculated according to Colby's formula are set forth below in table I.

TABLE I

Percent rice blast control of DC-A and DC-B and SC-E when applied alone or in mixture as found in the experiment and as expected using COLBY's formula

| Formulation | dose (g/ha) | efficacy (%) obtained | efficacy (%) expected |
|---|---|---|---|
| DC-A | 200 | 24 | — |
| DC-A | 400 | 65 | — |
| DC-B | 200 | 28 | — |
| DC-B | 400 | 61 | — |
| SC-E | 100 | 18 | — |
| SC-E | 200 | 41 | — |
| DC-A + SC-E | 200 + 100 | 84 | 38 |
| DC-A + SC-E | 400 + 100 | 87 | 72 |
| DC-B + SC-E | 200 + 100 | 73 | 41 |
| DC-B + SC-E | 400 + 100 | 76 | 68 |

Example 2 Control of *Rhizoctonia solani*

Infection with *Rhizoctonia solani*:

Three hours after the second application of the compounds/compounds mixtures, the plants were inoculated with *Rhizoctonia solani* (gown in rice grain-hull medium) by evenly sprinkling the inoculum on the soil surface at the basis of the plants. Plants were then placed into a moist chamber for 24 h. After that the plants were moved outdoors until the rice sheath blight disease could be evaluated.

The formulation applied, the dose rates of the active ingredients applied (expressed in grams of active ingredient per hectare), the results expressed as efficacy of disease control and the expected efficacies calculated according to Colby's formula are set forth below in table II.

Disease symptoms (rice blast and rice sheath blight) were assessed 7 days days after the second application (DAT) of the products.

TABLE II

Percent rice sheath blight control of DC-A and DC-B and SC-E when applied alone or in mixture as found in the experiment and as expected using COLBY's formula

| Formulation | dose (g/ha) | efficacy (%) rice sheath blight obtained | efficacy (%) rice sheath blight expected |
|---|---|---|---|
| DC-A | 200 | 45 | — |
| DC-A | 400 | 87 | — |
| DC-B | 200 | 75 | — |
| DC-B | 400 | 85 | — |
| SC-E | 100 | 18 | — |
| SC-E | 200 | 23 | — |
| DC-A + SC-E | 200 + 100 | 88 | 55 |
| DC-A + SC-E | 400 + 100 | 89 | 89 |
| DC-B + SC-E | 200 + 100 | 98 | 79 |
| DC-B + SC-E | 400 + 100 | 95 | 88 |

Example 3 Control of *Pyricularia oryzae*

For another experiment, established in the field in Japan paddy-rice plants of the variety "Koshihikari" were grown up in nursery boxes, and were transplanted to the field in plots of 10 sqm. 46 and 53 days after transplanting, the plants were sprayed with the formulations SC-A and SC-E and a in-tank mixture of these formulations after dilution in water and applying the equivalent of 1 liter per plot with a spraying equipment. The compound A was formulated as a 100 g/l SC.

Each treatment was applied in three plots (3 replicates). There were also untreated plots. 15 days after the second treatment 17% of the leaf area of the untreated rice plants (controls) were infected with the rice blast disease. The disease level (% infected leaf area) was also assessed in the treated plants, and the efficacy (in %) of the treatment was measured. The effects of mixtures according to the invention and the solo compounds are given in Table III.

TABLE III

Percent rice blast control of SC-A and SC-E when applied alone or in mixture as found in the experiment and as expected using COLBY's formula

| Formulation | dose (g/ha) | efficacy (%) rice sheath blight | |
| --- | --- | --- | --- |
| | | obtained | expected |
| SC-A | 50 | 41 | — |
| SC-A | 100 | 71 | — |
| SC-A | 200 | 72 | — |
| SC-E | 100 | 83 | — |
| SC-E | 150 | 91 | — |
| SC-E | 200 | 93 | — |
| SC-A + SC-E | 50 + 100 | 96 | 90 |
| SC-A + SC-E | 100 + 100 | 97 | 95 |
| SC-A + SC-E | 50 + 150 | 95 | 95 |

Example 4 Control of *Pyricularia oryzae*

Rice variety IAC-165 was direct seeded in field plots in Brazil. Individual field plots were 9 m$^2$ and each treatment was replicated 3 times. Overhead irrigation was used to ensure uniform germination and disease development but an artificial inoculation was not necessary as sufficient disease established itself naturally.

Two applications of each treatment were made, 7 days apart and in a water volume of 1000 l/ha. A visual assessment of disease control was made 14 days after the first application.

The effects of mixtures according to the invention (SC-D+SC-E) and the solo compounds are given in Table IV.

TABLE IV

Percent rice blast control of SC-D and SC-C when applied alone or in mixture as found in the experiment and as expected using COLBY's formula

| Formulation | dose (g/ha) | efficacy (%) | |
| --- | --- | --- | --- |
| | | obtained | expected |
| SC-D | 30 | 8 | — |
| SC-E | 100 | 4 | — |
| SC-D + SC-E | 30 + 100 | 29 | 12 |

Results:

The results given in tables I to IV show that mixtures of MBIs, such as phenoxyamides, and azolopyrimidines exhibit synergism.

What is claimed is:

1. A fungicidal composition comprising an acceptable carrier and/or surface active agent and synergistically effective amounts of
    (a) 5-chloro-6-(2,4,6-trifluorophenyl)-7-(1,1,1-trifluoroprop-2-ylamino)-[1,2,4]triazolo[1,5-a]pyrimidine; and
    (b) N-(1-cyano-1,2-dimetlyl-propyl)-2-(2,4-dichlorophenoxy)-propionamide.

2. A fungicidal composition according to claim 1 wherein the ratio (by weight) of 5-chloro-6-(2,4,6-trifluorophenyl)-7-(1,1,1-trifluoroprop-2-ylamino)-[1,2,4]triazolo[1,5-a]pyrimidine (a) to N-(1-cyano-1,2-dimethyl-propyl)-2-(2,4-dichlorophenoxy)-propionamide (b) is from 0.1:1 to 10:1.

3. A method of controlling rice diseases at a locus which comprises applying synergistically fungicidally effective amounts of:
    (a) 5-chloro-6-(2,4,6-trifluorophenyl)-7-(1,1,1-trifluoroprop-2-ylamino)-[1,2,4]triazolo[1,5-a]pyrimidine; and
    (b) N-(1-cyano-1,2-dimethyl-propyl)-2-(2,4-dichlorophenoxy)-propionamide to the locus.

4. A method according to claim 3 wherein the rice disease is selected from rice blast and rice sheath blight.

* * * * *